United States Patent [19]

Schade et al.

[11] Patent Number: 4,894,381

[45] Date of Patent: Jan. 16, 1990

[54] MICROBICIDAL (AZOLYL-VINYL)-PHENOL ALKENYL ETHERS

[75] Inventors: Gerold Schade, Cologne; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 204,471

[22] Filed: Jun. 9, 1988

[30] Foreign Application Priority Data

Jun. 27, 1987 [DE] Fed. Rep. of Germany ....... 3721336
Apr. 15, 1988 [DE] Fed. Rep. of Germany ....... 3812483

[51] Int. Cl.$^4$ .................. A01N 43/653; A01N 43; A01N 50; C07D 233/60
[52] U.S. Cl. .................. 514/383; 514/399; 548/262; 548/335; 548/346
[58] Field of Search .................. 548/235, 262, 346; 514/383, 399

[56] References Cited

U.S. PATENT DOCUMENTS 4,328,348  5/1982  Ogata et al. .................. 548/335
4,780,471  10/1988 Maeda et al. .................. 548/341 X

FOREIGN PATENT DOCUMENTS 0149976  7/1985  European Pat. Off. .
0162359  11/1985 European Pat. Off. .
0255243  2/1988  European Pat. Off. .
2634511  2/1978  Fed. Rep. of Germany .
2656728  6/1978  Fed. Rep. of Germany .
3021467  12/1980 Fed. Rep. of Germany .
3500503  7/1985  Fed. Rep. of Germany .

OTHER PUBLICATIONS

*Chemical Abstracts,* 108:51138g (1988) [Kataoka, T., et al., *Nippon Noyaku Gakkaishi* 1987, 12(3), 445–53].
*Chemical Abstracts,* 103:196102x (1985) [Jpn. Kurai Tokkyo Koho JP 6075,480, 4/27/85].

*Primary Examiner*—Richard A. Schwartz
*Attorney, Agent, or Firm*—Sprung Horn Kramer & Woods

[57] ABSTRACT

Microbicidally effective (azolyl-vinyl)phenol alkenyl ethers of the formula

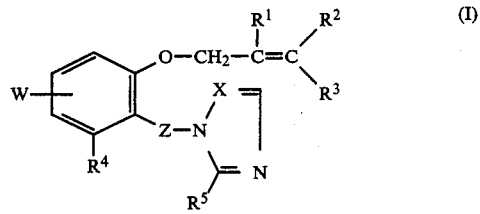

in which the various substituents are defined hereinbelow and addition products thereof with acids and metal salts.

7 Claims, No Drawings

MICROBICIDAL (AZOLYL-VINYL)-PHENOL ALKENYL ETHERS

The present invention relates to new (azolylvinyl)-phenol alkenyl ethers, a process for their preparation and their use as microbicides in plant protection and in the preservation of materials.

It is already known that numerous benzylimidazole derivatives can be used for combating fungi and bacteria (compare DE-OS (German Published Specification) 3,021,467, DE-OS (German Published Specification) 3,500,503 and European Published Specification 0,162,359). Thus, for example, 1-(1-[2-(thien-2-yl-methoxy)-phenyl]-vinyl)-imidazole, 1-(1-[2-(thien-2-yl-methoxy)-phenyl]-2,2-dimethyl-vinyl)-imidazole and 1-(1-[2-(3-chlorophenoxy-methoxy)-phenyl]-vinyl)-imidazole can be used as phytopathogenic fungi against fungicides. When low amounts are applied, however, the activity of these substances in some cases leaves something to be desired.

New (azolyl-vinyl)-phenol alkenyl ethers of the formula

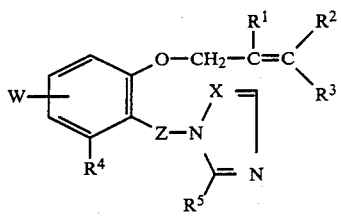
(I)

in which
R$^1$ represents hydrogen, halogen or alkyl,
R$^2$ represents hydrogen, halogen, alkyl, optionally substituted alkenyl or optionally substituted aryl, or
R$^1$ and R$^2$ together represent a C—C bond, thus forming an alkine bond between the carbon atoms which carry them,
R$^3$ represents hydrogen, halogen, alkyl or optionally substituted aryl,
R$^4$ represents hydrogen,
R$^5$ represents hydrogen or alkyl,
W represents hydrogen or halogen,
X represents nitrogen or a CH group and
Z represents the groupings

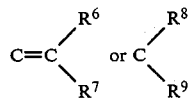

wherein
R$^6$ represents hydrogen, alkyl or optionally substituted phenyl, or
R$^6$ together with R$^4$ represents the grouping

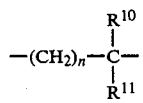

R$^7$ represents hydrogen or alkyl,
R$^8$ represents hydrogen or alkyl,
R$^9$ represents hydrogen or alkyl,
R$^{10}$ represents hydrogen or alkyl,
R$^{11}$ represents hydrogen or alkyl and
n represents the number 0, 1 or 2,
and acid addition salts and metal salt complexes thereof have now been found.

It has furthermore been found that (azolyl-vinyl)-phenol alkenyl ethers of the formula (I) and acid addition salts and metal salt complexes thereof are obtained by a process in which phenol derivatives of the formula

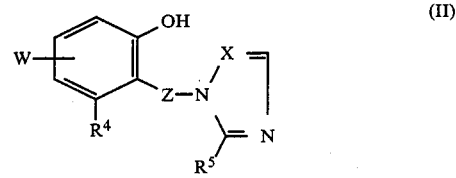
(II)

in which
R$^4$, R$^5$, W, X and Z have the abovementioned meaning,
are reacted with bases, if appropriate in the presence of a diluent, and the phenolates thereby formed, of the formula

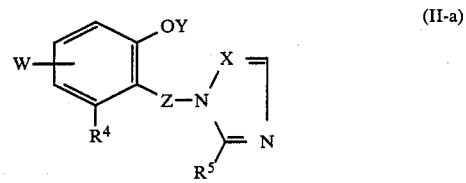
(II-a)

in which
R$^4$, R$^5$, W, X and Z have the abovementioned meaning and
Y represents a base radical,
are reacted with halogen compounds of the formula

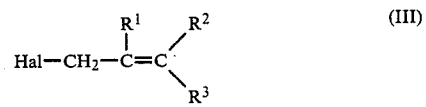
(III)

in which
R$^1$, R$^2$ and R$^3$ have the abovementioned meaning and
Hal represents chlorine, bromine or iodine,
in the presence of a diluent and if appropriate in the presence of an acid-binding agent, and, if appropriate, an acid or a metal salt is then added onto the compounds of the formula (I) thus obtained.

It has also been found that the new (azolyl-vinyl)-phenol alkenyl ethers of the formula (I) and acid addition salts and metal salt complexes thereof have very good microbicidal properties and can be used both in plant protection and in the preservation of materials.

Surprisingly, the substances according to the invention exhibit a clearly better activity in combating phytopathogenic fungi than 1-(1-[2-(thien-2-yl-methoxy)-phenyl]-vinyl)-imidazole, 1-(1-[2-thien-2-yl-methoxy)-phenyl]-2,2-dimethyl-vinyl)-imidazole and 1-(1-[2-(3-chlorophenoxy-methoxy)-phenyl]-vinyl)-imidazole, which are structurally similar already known compounds of the same type of action.

Formula (I) provides a general definition of the (azolyl-vinyl)-phenol alkenyl ethers according to the invention. Preferably, in this formula, $R^1$ represents hydrogen, fluorine, chlorine, bromine or alkyl with 1 to 4 carbon atoms, $R^2$ represents hydrogen, fluorine, chlorine, bromine, alkyl with 1 to 4 carbon atoms or alkenyl with 2 to 4 carbon atoms, it being possible for each of these alkenyl radicals to be substituted by optionally substituted aryl, or represents phenyl which is optionally substituted by one to three identical or different substituents from the group comprising alkyl with 1 to 4 carbon atoms, halogen and/or halogenoalkyl with 1 or 2 carbon atoms and 1 to 5 halogen atoms, or $R^1$ and $R^2$ together represent a C—C bond, thus forming an alkine bond between the carbon atoms which carry them, $R^3$ represents hydrogen, fluorine, chlorine, bromine, iodine or alkyl with 1 to 12 carbon atoms, or represents phenyl which is optionally substituted by one to three identical or different substituents from the group comprising alkyl with 1 to 4 carbon atoms, halogen and/or halogenoalkyl with 1 or 2 carbon atoms and 1 to 5 halogen atoms, $R^4$ represents hydrogen, $R^5$ represents hydrogen or alkyl with 1 to 4 carbon atoms, W represents hydrogen, fluorine, chlorine or bromine, X represents nitrogen or a CH group and Z represents the groupings

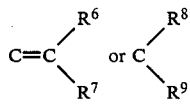

wherein $R^6$ represents hydrogen or alkyl with 1 to 4 carbon atoms, or represents phenyl which is optionally substituted by one to three identical or different substituents from the group comprising alkyl with 1 to 4 carbon atoms, halogen and/or halogenoalkyl with 1 or 2 carbon atoms and 1 to 5 halogen atoms, or $R^6$ together with $R^4$ represents the grouping

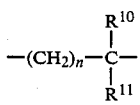

$R^7$ represents hydrogen or alkyl with 1 to 4 carbon atoms, $R^8$ represents hydrogen or alkyl with 1 to 4 carbon atoms, $R^9$ represents hydrogen or alkyl with 1 to 4 carbon atoms, $R^{10}$ represents hydrogen or alkyl with 1 to 4 carbon atoms, $R^{11}$ represents hydrogen or alkyl with 1 to 4 carbon atoms and n represents the number 0, 1 or 2.

Particularly preferred compounds of the formula (I) are those in which $R^1$ represents hydrogen, fluorine, chlorine, bromine, methyl, ethyl, n-propyl, isopropyl or n-butyl, $R^2$ represents hydrogen, fluorine, chlorine, bromine, methyl, ethyl, n-propyl, isopropyl, n-butyl, vinyl, propenyl or styryl, or represents phenyl which is optionally substituted by one to three identical or different substituents from the group comprising methyl, ethyl, fluorine, chlorine, bromine and/or trifluoromethyl, or $R^1$ and $R^2$ together represent a C—C bond, thus forming an alkine bond between the carbon atoms which carry them, $R^3$ represents hydrogen, fluorine, chlorine, bromine, iodine or alkyl with 1 to 10 carbon atoms, or represents phenyl which is optionally substituted by one to three identical or different substituents from the group comprising methyl, ethyl, fluorine, chlorine and/or trifluoromethyl, $R^4$ represents hydrogen, $R^5$ represents hydrogen, methyl or ethyl, W represents hydrogen or chlorine, X represents nitrogen or a CH group and Z represents the groupings

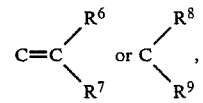

wherein $R^6$ represents hydrogen, methyl, ethyl, n-propyl, isopropyl or n-butyl, or represents phenyl which is optionally substituted by one to three identical or different substituents from the group comprising methyl, ethyl, fluorine, chlorine and/or trifluoromethyl, or $R^6$ together with $R^4$ represents the grouping

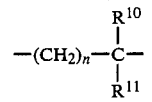

$R^7$ represents hydrogen, methyl, ethyl, n-propyl, isopropyl or n-butyl, $R^8$ represents hydrogen, methyl, ethyl, n-propyl, isopropyl or n-butyl, $R^9$ represents hydrogen, methyl, ethyl, n-propyl, isopropyl or n-butyl, $R^{10}$ represents hydrogen or methyl, $R^{11}$ represents hydrogen or methyl and n represents the number 0 or 1.

Addition products of acids and those (azolyl-vinyl)-phenol alkenyl ethers of the formula (I) in which $R^1$, $R^2$, $R^3$, $R^4$, $R^5$, W, X and Z have the meanings which have already been mentioned as preferred for these radicals are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main group II to IV and of sub-group I and II and IV to VIII of the periodic table of the elements and those (azolyl-vinyl)-phenol alkenyl ethers of the formula (I) in which $R^1$, $R^2$, $R^3$, $R^4$, $R^5$, W, X and Z have the meanings which have already been mentioned as preferred for these radicals are also preferred compounds according to the invention.

Salts of copper, zinc, manganese, magnesium, tin, iron and nickel are particularly preferred here. Possible anions of these salts are those which are derived from those acids which lead to physiologically tolerated addition products. Particularly preferred acids of this type are, in this connection, the hydrogen halide acids, such as, for example, hydrochloric acid and hydrobromic acid, and furthermore phosphoric acid, nitric acid and sulphuric acid.

The substances according to the invention can be in the form of cis- and trans-isomers, and in particular both in respect of the substituents on the alkenyl group and in the case where Z represents

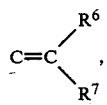

if $R^6$ and $R^7$ are different. The invention relates both to the pure cis- and trans-isomers and to their mixtures.

If 1-[1-(2-hydroxyphenyl)-vinyl]-imidazole is used as the starting substance, sodium hydroxide is used as the base and 1-chloro-2,3-dimethyl-but-2-ene is used as the reaction component, the course of the process according to the invention can be illustrated by the following equation:

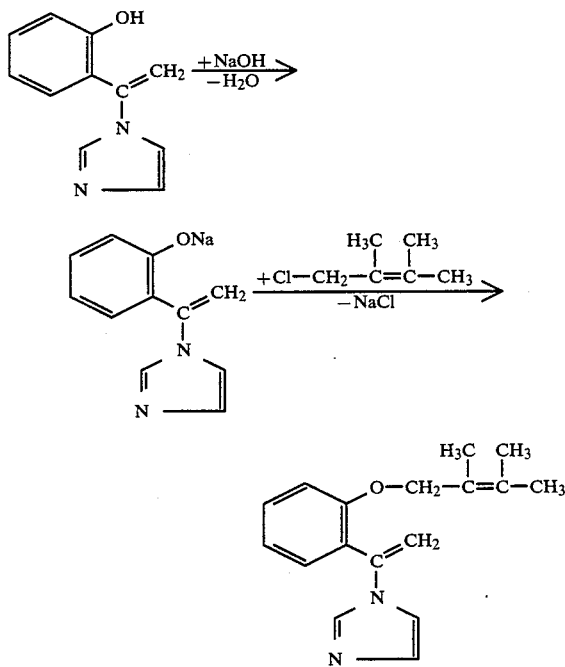

Formula (II) provides a general definition of the phenol derivatives required as starting substances for carrying out the process according to the invention. In this formula, $R^4$, $R^5$, W, X and Z preferably have those meanings which have already been mentioned as preferred for these radicals in connection with the description of the substances of the formula (I) according to the invention.

The phenol derivatives of the formula (II) are known or can be prepared by processes which are known in principle (compare J. Med. Chem. 27, 1142 (1984) and DE-OS (German Published Specification) 3,021,467).

Possible bases in carrying out the process according to the invention are all the strong bases customary for such reactions. Bases which can preferably be used are alkali metal hydroxides, alkali metal amides, alkali metal alcoholates, alkali metal hydrides, quaternary ammonium hydroxides or phosphonium hydroxides. Particularly preferred bases are sodium methylate, potassium tert.-butylate, sodium amide, sodium hydride and tetramethylammonium hydroxide. Y in formula (II-a) accordingly preferably represents an alkali metal cation, such as a sodium or potassium cation, or a quaternary ammonium or phosphonium cation.

Possible diluents in carrying out the first stage of the process according to the invention are all the organic solvents customary for such reactions. Solvents which can preferably be used are alcohols, such as methanol, ethanol, n-propanol, isopropanol, n-butanol and tert.-butanol.

The reaction temperatures can be varied within a substantial range in carrying out the first stage of the process according to the invention. The reaction is in general carried out at temperatures between 0° C. and 100° C., preferably between 10° C. and 60° C.

The first stage of the process according to the invention is in general carried out under normal pressure. However, it is also possible to carry out the reaction under increased or reduced pressure.

In carrying out the first stage of the process according to the invention, a procedure is in general followed in which 1 mol of base is employed per mol of phenol derivative. However, it is also possible for one or the other of the components to be used in excess. Working up is carried out by customary methods. A procedure is in general followed in which the reaction mixture is concentrated by stripping off the diluent and the phenolate which thereby remains is used either directly, or after prior purification, for the further synthesis.

Formula (III) provides a general definition of the halogen compounds used as reaction components in carrying out the second stage of the process according to the invention. In this formula, $R^1$, $R^2$ and $R^3$ preferably have those meanings which have already been mentioned as preferred for these radicals in connection with the description of the substances of the formula (I) according to the invention. Hal represents chlorine, bromine or iodine.

The halogen compounds of the formula (III) are known or can be prepared by processes which are known in principle.

Possible diluents in carrying out the second stage of the process according to the invention are all the organic solvents customary for such reactions. Solvents which can preferably be used are alcohols, such as methanol, ethanol and butanol, and furthermore ethers, such as diethyl ether, dioxane or tetrahydrofuran, and furthermore halogenated aliphatic hydrocarbons, such as methylene chloride, chloroform or carbon tetrachloride, and in addition nitriles, such as acetonitrile or propionitrile, and moreover amides, such as dimethylformamide, and highly polar solvents, such as dimethyl sulphoxide or hexamethylphosphoric acid triamide.

Possible acid-binding agents in carrying out the second stage of the process according to the invention are all the customary acid acceptors. Acid acceptors which can preferably be used are alkali metal carbonates and bicarbonates, such as sodium carbonate, potassium carbonate or sodium bicarbonate, and furthermore alkali metal hydroxides and alcoholates, such as sodium hydroxide, potassium hydroxide, sodium methylate or potassium tert.-butylate, and in addition tertiary aliphatic or aromatic amines, such as triethylamine, N,N-dimethylcyclohexyl-amine, N,N-dimethyl-benzylamine and pyridine, and in addition cyclic amines, such as 1,5-diaza-bicyclo[4.3.0]non-5-ene (DBN), 1,8-diaza-bicyclo[5.4.0]undec-7-ene (DBU) and 1,4-diaza-bicyclo[2.2.2]octane (DABCO).

The reaction temperatures can be varied within a substantial range in carrying out the second stage of the process according to the invention. The reaction is in general carried out at temperatures between 0° C. and 120° C., preferably between 10° C. and 100° C.

In carrying out the second stage of the process according to the invention, the reaction is in general carried out under normal pressure. However, it is also possible to carry out the reaction under increased or reduced pressure.

In carrying out the second stage of the process according to the invention, in general 1 to 1.3 mols of halogen compound of the formula (III) are employed per mol of phenolate of the formula (II-a). Working up is carried out by customary methods. A procedure is in general followed in which the reaction mixture is concentrated by stripping off the diluent, and the residue which remains is purified by recrystallization or by a chromatographic route.

The compounds of the formula (I) obtainable by the process according to the invention can be converted into acid addition salts or metal salt complexes.

Those acids which have already been mentioned as preferred acids in connection with the description of the acid addition salts according to the invention can preferably be used to prepare acid addition salts of the compounds of the formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above can preferably be used to prepare metal salt complexes of the compounds of the general formula (I).

The metal salt complexes of compounds of the general formula (I) can be obtained in a simple manner by customary processes, thus, for example, by dissolving the metal salt in alcohol, for example ethanol, and adding the solution to the compounds of the general formula (I). The metal salt complexes can be isolated in a known manner, for example by filtration, and if appropriate purified by recrystallization.

The active compounds according to the invention have a powerful microbicidal action and can be used as fungicides in plant protection and in the preservation of materials.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, *Xanthomonas oryzae*; Pseudomonas species, such as, for example, *Pseudomonas lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In plant protection, the substances according to the invention exhibit a particularly good action against *Fusarium fungi* and against Pyricularia and Botrytis. They also have powerful bactericidal properties and prove to be very effective in the agar plate test.

In the preservation of materials, the active compounds according to the invention can be used to preserve industrial materials. Industrial materials in this connection are to be understood as non-living materials which have been prepared for use in industry. Industrial materials which are to be protected from microbial change or destruction by the active compounds according to the invention can be, for example, adhesives, sizes, paper, card, textiles, leather, wood, paints, articles made of plastic, cooling lubricants and other materials which can be attacked or decomposed by microorganisms. In the context of the materials to be preserved, components of production lines, for example cooling water circulations, which can be impaired by multiplication of microorganisms, may also be mentioned. Industrial materials which may be mentioned as preferred in the context of the present invention are adhesives, sizes, paper and card, leather, wood, paints, cooling lubricants and cooling circulations, particularly preferably wood.

Examples which may be mentioned of microorganisms which can cause degradation to or a change in the industrial materials are bacteria, fungi, yeasts, algae and slime organisms. The active compounds according to the invention preferentially act against fungi, in particular molds, fungi which discolor and destroy wood (Basidiomycetes), and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pitophila*, Trichoderma, such as *Trichoderma viride*, Escherichia, such as *Escherichia coli*, Pseudomonas, such as *Pseudomonas aeruginosa* and Staphylococcus, such as *Staphylococcus aureus*.

The active compounds according to the invention can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or the use forms prepared therefrom by further dilution, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the substances according to the invention are used as fungicides, the amount applied can be varied within a substantial range depending on the nature of the administration. Thus, in the treatment of parts of plants, the active compound concentrations in the use forms can in general be between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and the use of the active compounds according to the invention is illustrated by the following examples.

Preparation Examples

EXAMPLE 1

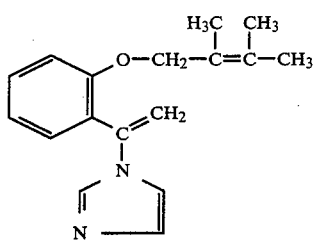
(1)

9.2 g (0.23 mol) of sodium hydroxide are added to a mixture of 39.1 g (0.21 mol) of 1-[1-(2-hydroxyphenyl)-vinyl]-imidazole and 200 ml of methanol at room temperature, with stirring. When the addition has ended, the mixture is stirred at 50° C. for a further 30 minutes and is then concentrated under reduced pressure by stripping off the solvent. The solid residue which remains is taken up in 200 ml of dimethylformamide. 24.9 g (0.21 mol) of 1-chloro-2,3-dimethyl-but-2-ene are added to the solution formed at a temperature of 25° C., with stirring. The reaction mixture is stirred at 20° C. for a further 12 hours and then worked up by being concentrated by stripping off the diluent. The residue obtained is chromatographed over silica gel. 35.5 g (63% of theory) of 1-[1-(2-(2,3-dimethyl-but-2-en-1-yl-oxy)phenyl)-vinyl]-imidazole in the form of an oil are obtained in this manner.

$^1$H-NMR (DMSO):
$\delta = 4.38$ ppm (s) [O—CH$_2$—C=C]

The substances of the formula

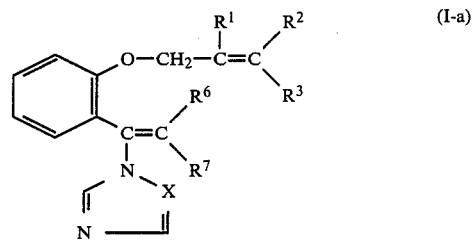
(I-a)

listed in the following Table 1 are also obtained by the method described in Example 1.

TABLE 1

| Example | R$^1$ | R$^2$ | R$^3$ | R$^6$ | R$^7$ | X | $^1$H—NMR (DMSO) $\delta$ (O—CH$_2$—C=C) |
|---|---|---|---|---|---|---|---|
| 2 | C—C—Bond | | H | H | H | CH | 4.56 (d) |
| 3 | H | H | H | H | H | CH | 4.40 (d) |
| 4 | CH$_3$ | H | H | H | H | CH | 4.30 (s) |
| 5 | H | H | —CH$_2$—C(CH$_3$)(CH$_3$)—CH$_2$—C(CH$_3$)$_3$ | H | H | CH | 4.39 (d) |
| 6 | H | CH$_3$ | CH$_3$ | H | H | CH | 4.38 (d) |
| 7 | Cl | H | H | H | H | CH | 4.43 (s) |
| 8 | Cl | Cl | Cl | H | H | CH | 4.74 (s) |
| 9 | H | Cl | Cl | H | H | CH | 4.58 (d) |
| 10 | Br | H | H | H | H | CH | 4.65 (s) |
| 11 | H | Cl | CH$_3$ | H | H | CH | 4.47 (d), 4.53 (d) |
| 12 | H | H | H | CH$_3$ | H | CH | 4.42 (m), 4.47 (m) |
| 13 | CH$_3$ | H | H | CH$_3$ | H | CH | 4.4 (s) |
| 14 | Cl | Cl | Cl | CH$_3$ | H | CH | 4.84 (s), 4.90 (s) |
| 15 | H | CH$_3$ | CH$_3$ | CH$_3$ | H | CH | 4.37 (d), 4.41 (d) |
| 16 | CH$_3$ | CH$_3$ | CH$_3$ | CH$_3$ | H | CH | 4.42 (s), 4.43 (s) |
| 17 | H | CH$_3$ | CH$_3$ | CH$_3$ | CH$_3$ | CH | 4.46 (d) |
| 18 | CH$_3$ | CH$_3$ | CH$_3$ | CH$_3$ | CH$_3$ | CH | 4.46 (s) |
| 19 | Cl | Cl | Cl | CH$_3$ | CH$_3$ | CH | 4.76 (s) |
| 20 | H | H | H | CH$_3$ | CH$_3$ | CH | 4.43 (d) |
| 21 | CH$_3$ | H | H | CH$_3$ | CH$_3$ | CH | 4.35 (d) |
| 22 | Cl | H | H | CH$_3$ | CH$_3$ | CH | 4.68 (s) |
| 23 | Cl | H | H | CH$_3$ | H | CH | 4.42 (t), 4.44 (t) |
| 24 | C—C—Bond | | I | H | H | CH | 4.81 (s) |
| 25 | H | H | H | H | H | N | 4.40 (d) |
| 26 | CH$_3$ | H | H | H | H | N | 4.31 (s) |
| 27 | H | CH$_3$ | CH$_3$ | H | H | N | 4.40 (d) |
| 28 | CH$_3$ | CH$_3$ | CH$_3$ | H | H | N | 4.39 (s) |
| 29 | Cl | H | H | H | H | N | 4.44 (s) |
| 30 | Cl | Cl | Cl | H | H | N | 4.83 (s) |
| 31 | H | H | H | C$_6$H$_5$ | H | CH | 4.52 (d) |
| 32 | CH$_3$ | H | H | C$_6$H$_5$ | H | CH | 4.46 (s) |
| 33 | H | CH$_3$ | CH$_3$ | C$_6$H$_5$ | H | CH | 4.49 (d) |
| 34 | CH$_3$ | CH$_3$ | CH$_3$ | C$_6$H$_5$ | H | CH | 4.50 (s) |
| 35 | Cl | H | H | C$_6$H$_5$ | H | CH | 4.72 (s) |
| 36 | Br | H | H | C$_6$H$_5$ | H | CH | 4.77 (s) |
| 37 | H | C$_6$H$_5$ | H | H | H | CH | 4.61 (d) |

The substances of the formula

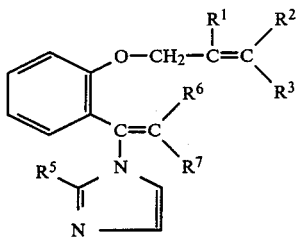 (I-b)

listed in the following Table 2 are also obtained by the method described in Example 1.

TABLE 2

| Example Nr. | $R^1$ | $R^2$ | $R^3$ | $R^5$ | $R^6$ | $R^7$ | $^1$H—NMR (DMSO) δ (O—CH$_2$—C═C |
|---|---|---|---|---|---|---|---|
| 38 | H | H | H | CH$_3$ | H | H | 4.45 (m) |
| 39 | Br | H | H | CH$_3$ | H | H | 4.70 (s) |
| 40 | Cl | H | H | CH$_3$ | H | H | 4.64 (s) |
| 41 | CH$_3$ | H | H | CH$_3$ | H | H | 4.38 (s) |
| 42 | CH$_3$ | CH$_3$ | CH$_3$ | CH$_3$ | H | H | 4.40 (s) |
| 43 | H | CH$_3$ | CH$_3$ | CH$_3$ | H | H | 4.42 (d) |

The substances of the formula

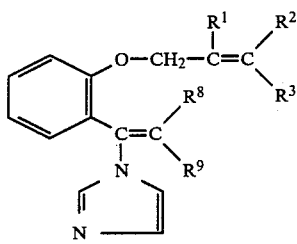 (I-c)

listed in the following Table 3 are also obtained by the method described in Example 1.

TABLE 3

| Example Nr. | $R^1$ | $R^2$ | $R^3$ | $R^8$ | $R^9$ | $^1$H—NMR (DMSO) δ (O—CH$_2$—C═C) |
|---|---|---|---|---|---|---|
| 44 | H | H | H | CH$_3$ | H | 4.59 (d) |
| 45 | CH$_3$ | H | H | CH$_3$ | H | 4.50 (s) |
| 46 | Cl | H | H | CH$_3$ | H | 4.75 (s) |
| 47 | H | CH$_3$ | CH$_3$ | CH$_3$ | H | 4.55 (d) |
| 48 | CH$_3$ | CH$_3$ | CH$_3$ | CH$_3$ | H | 4.52 (s) |
| 49 | Cl | Cl | Cl | CH$_3$ | H | 5.02 (s) |

The substances of the formula

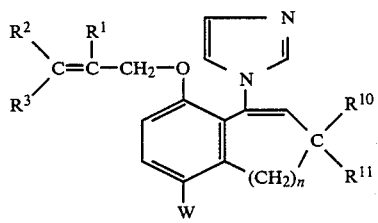 (I-d)

listed in the following Table 4 are also obtained by the method described in Example 1.

TABLE 4

| Example Nr. | $R^1$ | $R^2$ | $R^3$ | $R^{10}$ | $R^{11}$ | n | W | $^1$H—NMR (DMSO) δ (O—CH$_2$—C═C) |
|---|---|---|---|---|---|---|---|---|
| 50 | H | H | H | H | H | 1 | H | 4.25 (d) |
| 51 | H | CH$_3$ | CH$_3$ | H | H | 1 | H | 4.19 (d) |
| 52 | Cl | H | H | H | H | 1 | H | 4.35 (s) |
| 53 | H | CH$_3$ | CH$_3$ | CH$_3$ | CH$_3$ | 0 | Cl | 4.43 (d) |
| 54 | Cl | H | H | CH$_3$ | CH$_3$ | 0 | Cl | 4.60 (s) |

Preparation of starting substances:

EXAMPLE 55

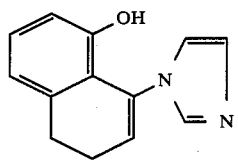

227 g (1.9 mols) of thionyl chloride are added dropwise to a mixture of 503 g (7.4 mols) of imidazole and 1.6 liter of methylene chloride at 5° C., while stirring. The mixture is subsequently stirred for 20 minutes and 157 g (0.97 mol) of 8-hydroxy-1-tetralone are then added. The reaction mixture is stirred for a further 2 hours and then filtered and the filtrate is poured into ice water. The organic phase is separated off and concentrated under reduced pressure. The residue is taken up in 1 liter of toluene and the solution formed is boiled under reflux for one hour. The mixture is concentrated again under reduced pressure and the residue which remains is dissolved in methylene chloride. The organic phase is washed with water and concentrated under reduced pressure. The residue is triturated with toluene, the product separating out as crystals. 95 g of 3,4-dihydro-1-(imidazol-1-yl)-8-hydroxynaphthalene of melting point 186° C. are obtained in this manner.

EXAMPLE 56

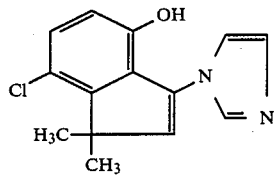

1-(Imidazol-1-yl)-3,3-dimethyl-4-chloro-7-hydroxy-indene in the form of colorless crystals is prepared from 3,3-dimethyl-4-chloro-7-hydroxy-indanone by the method described in Example 55.

The substances of the formula

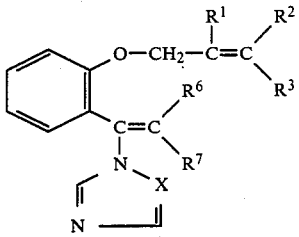 (I-a)

listed in the following Table 5 are also obtained by the method described in Example 1.
TABLE 5
| Expl. | R¹ | R² | R³ | R⁶ | R⁷ | X | ¹H—NMR (DMSO) δ (O—CH₂—C≡C) |
|---|---|---|---|---|---|---|---|
| 57 | H | 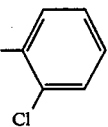 2-Cl-C₆H₄ | H | H | H | CH | 4.68 (d) |
| 58 | H | 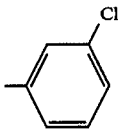 3-Cl-C₆H₄ | H | H | H | CH | 4.61 (d) |
| 59 | H | 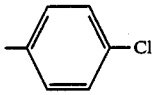 4-Cl-C₆H₄ | H | H | H | CH | 4.58 (s) |
| 60 | H | 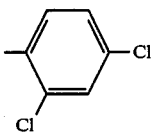 2,4-Cl₂-C₆H₃ | H | H | H | CH | 4.68 (d) |
| 61 | H | 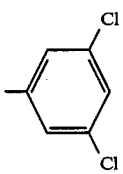 3,5-Cl₂-C₆H₃ | H | H | H | CH | 4.61 (d) |
| 62 | H | 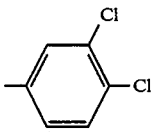 3,4-Cl₂-C₆H₃ | H | H | H | CH | 4.61 (d) |
| 63 | H | 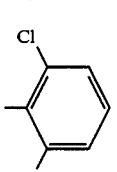 2,6-Cl₂-C₆H₃ | H | H | H | CH | 4.71 (d) |
| 64 | H | 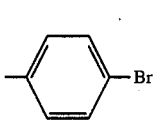 4-Br-C₆H₄ | H | H | H | CH | 4.58 (d) |
| 65 | H | 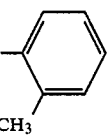 2-CH₃-C₆H₄ | H | H | H | CH | 4.63 (d) |
| 66 | H | 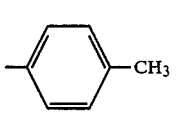 4-CH₃-C₆H₄ | H | H | H | CH | 4.57 (d) |

TABLE 5-continued

| Expl. | R¹ | R² | R³ | R⁶ | R⁷ | X | ¹H—NMR (DMSO) δ (O—CH₂—C=C) |
|---|---|---|---|---|---|---|---|
| 67 | H | 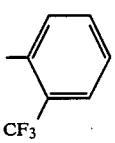 |  | H | H | H | CH | 4.70 (d) |
| 68 | H | 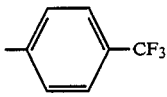 |  | H | H | H | CH | 4.65 (d) |

The compounds shown below were employed as comparison substances in the following use examples.

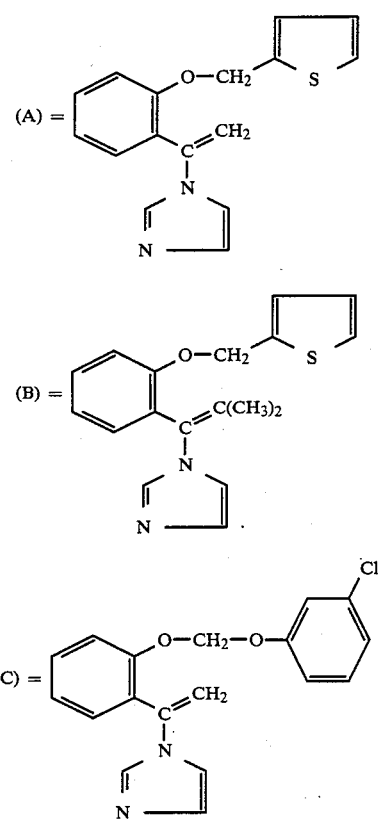

EXAMPLE A

Botrytis test (beans)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, the substance 1 and 16 according to the invention exhibit a considerably better activity than comparison substances A and B.

EXAMPLE B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, substances 2, 6, 7, 8, 9, 10, 12, 15, 16, 18, 46 and 49 according to the invention exhibit a considerably better action than comparison substance C.

It will be appreciated that the instant specification and claims are set forth by way of illustration and not limitation, and that various modifications and changes may be made without departing from the spirit and scope of the present invention.

What is claimed is:

1. An (azolyl-vinyl)-phenol alkenyl ether, or acid or metal salt addition product thereof, of the formula

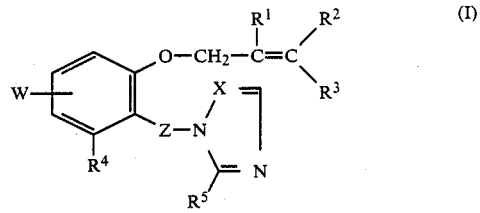

in which
R¹ represents hydrogen, fluorine, chlorine, bromine or alkyl with 1 to 4 carbon atoms,
R² represents hydrogen, fluorine, chlorine, bromine, alkyl with 1 to 4 carbon atoms, or alkenyl with 2 to 4 carbon atoms optionally substituted by optionally substituted aryl, or represents phenyl which is optionally substituted by one to three identical or different substituents from the group consisting of alkyl with 1 to 4 carbon atoms, halogen and/or halogenoalkyl with 1 or 2 carbon atoms and 1 to 5 halogen atoms, or $R^1$ and $R^2$ together represent a C—C bond, thus forming an alkine bond between the carbon atoms which carry the, $R^3$ represents hydrogen, fluorine, chlorine, bromine, iodine or alkyl with 1 to 12 carbon atoms, or represents phenyl which is optionally substituted by one to three identical or different substituents from the group consisting of alkyl with 1 to 4 carbon atoms, halogen and/or halogenoalkyl with 1 or 2 carbon atoms and 1 to 5 halogen atoms, $R^4$ represents hydrogen, $R^5$ represents hydrogen or alkyl with 1 to 4 carbon atoms, W represents hydrogen, fluorine, chlorine or bromine, X represents nitrogen or a CH group and Z represents the groupings

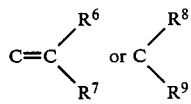

wherein $R^6$ represents phenyl which is optionally substituted by one to three identical or different substituents from the group consisting of alkyl with 1 to 4 carbon atoms, halogen and/or halogenoalkyl with 1 or 2 carbon atoms and 1 to 5 halogen atoms, or $R^6$, together with $R^4$, represents the grouping

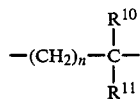

$R^7$ represents hydrogen or alkyl with 1 to 4 carbon atoms, $R^8$ represents hydrogen or alkyl with 1 to 4 carbon atoms, $R^9$ represents hydrogen or alkyl with 1 to 4 carbon atoms, $R^{10}$ represents hydrogen or alkyl with 1 to 4 carbon atoms, $R^{11}$ represents hydrogen or alkyl with 1 to 4 carbon atoms and n represents the number 0, 1 or 2.

2. An (azolyl-vinyl)-phenol alkenyl ether or addition product thereof according to claim 1, in which $R^1$ represents hydrogen, fluorine, chlorine, bromine, methyl, ethyl, n-propyl, isopropyl or n-butyl, $R^2$ represents hydrogen, fluorine, chlorine, bromine, methyl, ethyl, n-propyl, isopropyl, n-butyl, vinyl, propenyl or styryl, or represents phenyl which is optionally substituted by one to three identical or different substituents from the group consisting of methyl, ethyl, fluorine, chlorine, bromine and/or trifluoromethyl, or $R^1$ and $R^2$ together represent a C—C bond, thus forming an alkine bond between the carbon atoms which carry them, $R^3$ represents hydrogen, fluorine, chlorine, bromine, iodine or alkyl with 1 to 10 carbon atoms, or represents phenyl which is optionally substituted by one to three identical or different substituents from the group consisting of methyl, ethyl, flurine, chlorine and/or trifluoromethyl, $R^4$ represents hydrogen, $R^5$ represents hydrogen, methyl or ethyl, W represents hydrogen or chlorine, X represents nitrogen or a CH group and Z represents the groupings

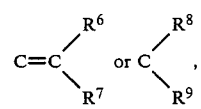

wherein $R^6$ represents phenyl which is optionally substituted by one to three identical or different substituents from the group consisting of methyl, ethyl, fluorine, chlorine and/or trifluoromethyl, or $R^6$ together with $R^4$ represents the grouping

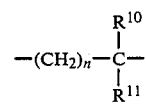

$R^7$ represents hydrogen, methyl, ethyl, n-propyl, isopropyl or n-butyl, $R^8$ represents hydrogen, methyl, ethyl, n-propyl, isopropyl or n-butyl, $R^9$ represents hydrogen, methyl, ethyl, n-propyl, isopropyl or n-butyl, $R^{10}$ represents hydrogen or methyl, $R^{11}$ represents hydrogen or methyl and n represents the number 0 or 1.

3. A compound according to claim 1, wherein such compound is 1-[1-(2-(3-methyl-but-2-en-1-yl-oxy)-phenyl)-2-phenyl-vinyl]-imidazole of the formula

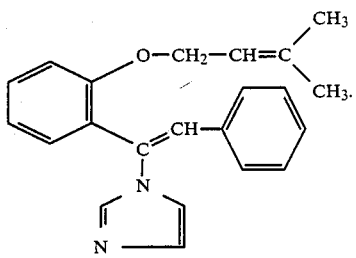

4. A compound according to claim 1, wherein such compound is 1-[1-(2-(2-bromoallyloxy)-phenyl)-2-phenylvinyl]-imidazole of the formula

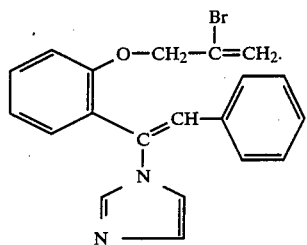

5. A microbicidal composition comprising a microbicidally effective amount of a compound or addition product thereof according to claim 1 and a diluent.

6. A method of combating microbes which comprises applying to such microbes or to a locus from which it is desired to exclude such microbes a microbicidally effective amount of a compound or addition product thereof according to claim 1.

7. The method according to claim 6, wherein such compound is

1-[1-(2-(3-methyl-but-2-en-1-yl-oxy)-phenyl)-2-phenylvinyl]-imidazole, or

1-[1-(2-(2-bromoallyloxy)-phenyl)-2-phenylvinyl]-imidazole, or an addition product thereof with an acid or metal salt.

* * * * *